United States Patent [19]

Carchidi

[11] Patent Number: 5,690,489
[45] Date of Patent: Nov. 25, 1997

[54] DELIVERY AND DRIVE TOOL FOR THREADED MEMBERS AND METHOD FOR USE

[76] Inventor: Joseph Edward Carchidi, 132 Samuel Ave., West Bridgewater, Mass. 02379

[21] Appl. No.: 507,086

[22] Filed: Jul. 26, 1995

[51] Int. Cl.$^6$ ............................................. A61C 3/00
[52] U.S. Cl. ..................... 433/141; 433/174; 81/436; 606/104
[58] Field of Search ........................... 433/173, 174, 433/141; 606/104; 81/44, 55, 443, 451, 436

[56] References Cited

U.S. PATENT DOCUMENTS

| | | | |
|---|---|---|---|
| 1,227,391 | 5/1917 | Cooper | 81/443 X |
| 2,458,391 | 1/1949 | Lavietes | 81/436 |
| 4,856,994 | 8/1989 | Lazzara et al. | |
| 5,105,690 | 4/1992 | Lazzara et al. | 81/436 |

*Primary Examiner*—Jeffrey A. Smith
*Attorney, Agent, or Firm*—John A. Haug

[57] ABSTRACT

A self-locking cylindrical drive (10,10') to deliver and assemble internally hexed prosthetic components such as screws and abutments into place is shown. The head (14) of the tool engages and locks with the flat side surfaces of the internally hexed prosthetic component. The tool (10,10') allows for extra-oral assembly of a component with the tool to minimize any risk of a component falling off or being lost in a patient's mouth during delivery of the component. Final seating of the component is then accomplished using a conventional hexagonal drive tool with appropriate delivery torque. The tool is formed into both a standard hand driven wrench (10) and contra-angle drill (10').

6 Claims, 1 Drawing Sheet

DELIVERY AND DRIVE TOOL FOR THREADED MEMBERS AND METHOD FOR USE

BACKGROUND OF THE INVENTION

1. Field of the Invention

This invention relates generally to tools used to deliver and drive threaded members and more particularly to surgical and prosthetic tools used to deliver and assemble dental implant components such as screws and abutments.

2. Description of Related Art

The present invention addresses a problem associated with the delivery and assembly of a prosthetic component such as an abutment or screw using an internal hexagon to drive and seat the component. Since a conventional or standard external hexagonal tool, i.e., Allen wrench, is manufactured and toleranced to passively fit and drive a mating hexagonal screw or abutment, there exists a danger for the component to fall off during delivery to the intended site of installation. Without a secure assembly of the component to the hexagonal tool a doctor attempting to place a prosthetic component into a patient's mouth runs the risk of having the component drop off in a patient's mouth or be lost during a surgical procedure.

One attempt to remedy this functional deficiency comprised applying a frictional locking taper to the flats of the hexagonal wrench and socket which allowed the tool to use friction to lock the internal tapered hexagonal recess of the screw or abutment onto the flat surfaces of the wrench as described in U.S. Pat. No. 4,856,994. Although this addressed the problem of the component prematurely separating from the tool, it is expensive to make such tools since the taper must be milled into the wrench as well as the socket of the component.

SUMMARY OF THE INVENTION

It is an object of the present invention to provide a tool to deliver prosthetic components such as screws and abutments to their mating sites and disengage the components only after the components are threaded to their intended seat which overcomes the expense limitations of the prior art noted above. A conventional hexagonal tool can then be used to tighten and lock the components into place. Another object of the invention is to provide a tool that can be cost effectively manufactured using conventional machinery. Yet another object is the provision of a method for delivering a threaded prosthetic component having a conventional hexagonally formed recess to a selected threaded bore and for driving the component into the threaded bore.

Briefly, in accordance with the invention, a cylindrical post tool is formed with a self-locking cylindrical tapered head that will frictionally engage and lock into the recess of internal hexagonal dental implant screws and abutments. In a first embodiment the tool is provided with an enlarged diameter portion at an opposite end to facilitate use as a hand tool while in a modified embodiment an attachment surface is provided for use with conventional power drill apparatus.

BRIEF DESCRIPTION OF THE DRAWINGS

Other objects, advantages and details of the novel and improved prosthetic component tool of the invention appear in the following detailed description of preferred embodiments of the invention, the detailed description referring to the drawings in which.

DESCRIPTION OF PREFERRED EMBODIMENTS

Figure 1:
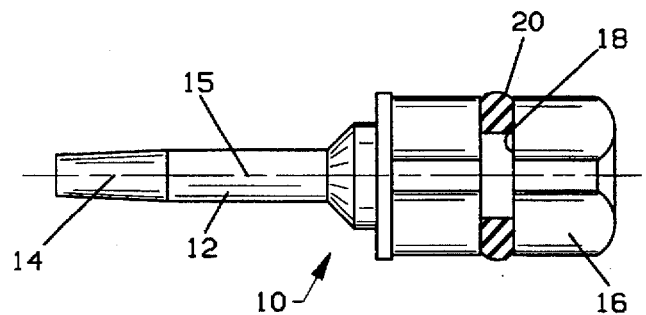
FIG. 1 is a plan view of a hand driven delivery tool made in accordance with the invention.

Referring to FIG. 1, a hand driven cylindrical tool 10 made in accordance with the invention comprises a generally elongated member having opposite end portions having a straight cylindrical neck 12 and having at one end a self-locking cylindrical tapered delivery and driving head 14. This self-locking tapered head 14 is formed having an angle with the longitudinal axis 15 of the cylindrical tool of less than approximately three degrees and having an appropriate diameter at the larger and smaller ends of the tapered section to frictionally lock into the recess of internal hexagonal portions of prosthetic components such as abutments and screws and release once the component is driven down and met by torsional resistance. At the opposite end of the tool member an enlarged diameter portion 16 is formed to serve as a hand or ratchet driven handle. If desired, a circumferential groove 18 can be provided with an annular resilient ring 20 placed therein to facilitate handling of tool 10.

Figure 2:
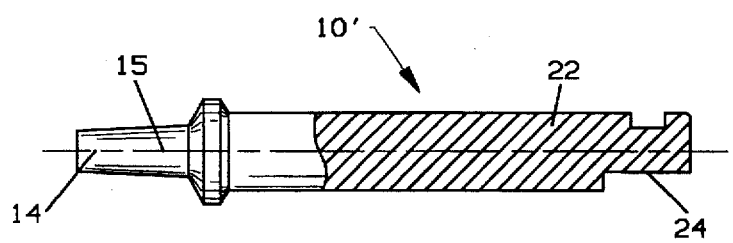
FIG. 2 is a view similar to FIG. 1 of a modified embodiment comprising a contra-angle handpiece delivery tool.

With reference to FIG. 2, a modified embodiment is shown comprising a cylindrical handpiece delivery drill member 10' using the self-locking cylindrical tapered delivery and driving head 14 made in accordance with the invention. Self-locking head 14 having an appropriate diameter at the larger and smaller ends of the tapered section will frictionally lock onto the flat surfaces formed in a hexagonal recess of abutments and screws and release once met with torsional resistance above a selected level involved in driving the component into a threaded bore. At the opposite end of drill member 10' a standard drill shank 22 having a suitable seating surface such as longitudinally extending flat surface 24 is formed for use with power drill apparatus.

Figure 3:
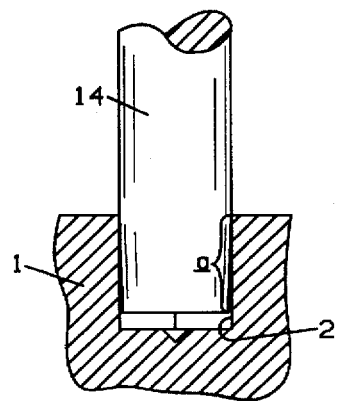
FIGS. 3 and 4 are broken away front and top views respectively of a prosthetic component and broken away delivery and driving head received in a hexagonal recess of the component.
Figure 4:
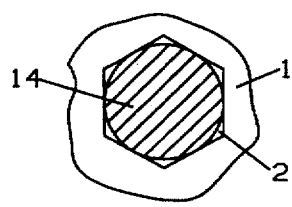

With reference to FIGS. 3 and 4, in both tool configurations the user simply assembles the self-locking tapered head 14 of the tool into the hexagonal recess 2 of prosthetic component 1 by pressing them together with finger pressure. Since the tapered cylindrical head 14 only holds onto the flat surfaces of the internal hexagonal recess of the prosthetic component at the outer edge thereof with point contacts, once the tool is met with torsional resistance above a selected level involved with driving the component into the threaded bore, i.e., upon bottoming out, the tool will easily release. Head 14 is formed with a diameter at length a from the distal free end thereof essentially equal to the distance between the flats of the hexagonal recess of the component with which the tool is to be used with length a selected to be less than the depth of recess 2 to prevent bottoming out of the tool prior to frictional engagement.

By way of example, a hand driven 1.25 mm hexagonal delivery tool 10 is effective having a taper angle with the longitudinal axis of the tool of approximately 2 degrees, 15 minutes starting from a distal free end of the tool having a diameter 0.0495/0.0485 inches while a 0.9 mm hexagonal drill tool 10' is effective with a taper angle of approximately 2 degrees, 45 minutes starting from a free distal end having a diameter of 0.0348/0.0388 inches. It will be understood that other angles of less than approximately 3 degrees can also be used effectively.

Tools made in accordance with the invention can conveniently be made in a conventional lathe due to their cylindrical configuration thereby making the tools cost effective. Further, tools made in accordance with the invention can be used with components having conventional hexagonal recesses. Such tools provide the dental implant professional with instruments which are easy to use, reliable yet which avoid the shortcomings of the prior art described above. It should be understood that this invention includes all modifications and equivalents of the described embodiments falling within the scope of the appended claims.

What is claimed:

1. A drive and delivery tool for use with a dental prosthetic component having a threaded portion and a recess formed with hexagonal flat side surfaces comprising a generally elongated member having a longitudinal axis and having opposite end portions, one end portion having a circular cross section at any given point along the longitudinal axis, the said one end portion having a cylindrical tapered surface adapted to be received in the recess of the component for frictional engagement with essentially only a point on respective flat side surfaces defining the recess.

2. A drive and delivery tool according to claim 1 in which the tool has a longitudinal axis and the tapered surface forms an angle with the longitudinal axis of less than approximately 3 degrees.

3. A drive and delivery tool according to claim 2 in which the opposite end portion has a longitudinally extending flat surface for use with power drill locking mechanisms.

4. A drive and delivery tool according to claim 2 in which the elongated member has a central portion with a selected circumference and the opposite end portion has an enlarged circumference to serve as a handle to facilitate manual use of the tool.

5. A method for delivering a threaded prosthetic component to a threaded bore, the component having a longitudinal axis and a recess formed at an end thereof, the recess having longitudinally extending flat side surfaces for receiving a tool for driving the component into the threaded bore, comprising the steps of taking an elongated member having a longitudinal axis and having opposite end portions having one end portion formed with a circular cross section at any given point along the longitudinal axis, a cylindrical locking taper on the one end portion, the taper extending from a first smaller diameter at a distal end of said one end portion to a second larger diameter spaced longitudinally from the distal end, the diameters selected so that the tapered surface frictionally engages essentially only with a point on each flat said surface when said one end is pressed into the recess, placing said one end portion in said recess, pressing said one end portion into the recess to lock said elongated member and said threaded prosthetic component together and delivering the threaded prosthetic component to a selected site.

6. A method according to claim 5 in which the taper forms an angle with the longitudinal axis of less than approximately 3 degrees.

* * * * *

(12) REEXAMINATION CERTIFICATE (4552nd)
United States Patent
Carchidi

(10) Number: US 5,690,489 C1
(45) Certificate Issued: Apr. 9, 2002

(54) DELIVERY AND DRIVE TOOL FOR THREADED MEMBERS AND METHOD FOR USE

(75) Inventor: Joseph Edward Carchidi, West Bridgewater, MA (US)

(73) Assignee: Ace Surgical Supply Co., Inc., Brockton, MA (US)

Reexamination Request:
No. 90/006,001, May 8, 2001

Reexamination Certificate for:
Patent No.: 5,690,489
Issued: Nov. 25, 1997
Appl. No.: 08/507,086
Filed: Jul. 26, 1995

(51) Int. Cl.[7] .................................................. A61C 3/00
(52) U.S. Cl. .......................... 433/141; 433/174; 81/436; 606/104
(58) Field of Search ................................. 433/141, 174, 433/173; 606/104; 81/44, 55, 443, 451, 436

(56) References Cited

U.S. PATENT DOCUMENTS 5,538,428 A 7/1996 Staubli

*Primary Examiner*—Cary E. O'Connor

(57) ABSTRACT

A self-locking cylindrical drive (10,10') to deliver and assemble internally hexed prosthetic components such as screws and abutments into place is shown. The head (14) of the tool engages and locks with the flat side surfaces of the internally hexed prosthetic component. The tool (10,10') allows for extra-oral assembly of a component with the tool to minimize any risk of a component falling off or being lost in a patient's mouth during delivery of the component. Final seating of the component is then accomplished using a conventional hexagonal drive tool with appropriate delivery torque. The tool is formed into both a standard hand driven wrench (10) and contra-angle drill (10').

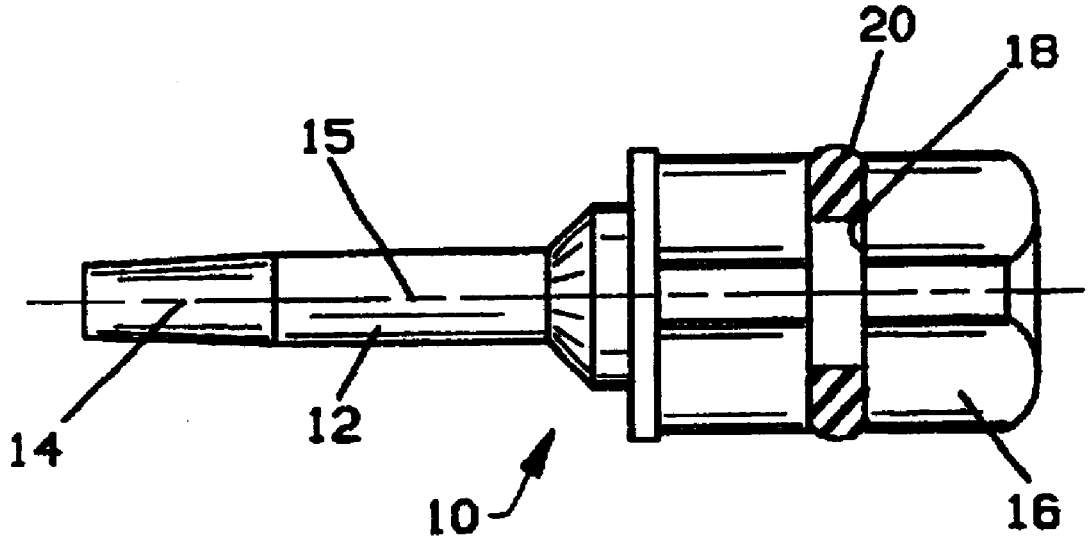

REEXAMINATION CERTIFICATE ISSUED UNDER 35 U.S.C. 307

NO AMENDMENTS HAVE BEEN MADE TO THE PATENT

AS A RESULT OF REEXAMINATION, IT HAS BEEN DETERMINED THAT:

The patentability of claims 1–6 is confirmed.

* * * * *